(12) United States Patent
Garrity et al.

(10) Patent No.: US 6,730,333 B1
(45) Date of Patent: May 4, 2004

(54) NUTRACEUTICAL MANGOSTEEN COMPOSITION

(75) Inventors: Aaron R. Garrity, Pleasant Grove, UT (US); Gordon A. Morton, Springville, UT (US); Joseph C. Morton, Springville, UT (US)

(73) Assignee: DBC, LLC, Draper, UT (US)

( * ) Notice: Subject to any disclaimer, the term of this patent is extended or adjusted under 35 U.S.C. 154(b) by 0 days.

(21) Appl. No.: 10/283,600

(22) Filed: Oct. 30, 2002

(51) Int. Cl.$^7$ .............................. A61K 35/78; A23L 2/00
(52) U.S. Cl. ........................ 424/777; 424/725; 426/599
(58) Field of Search ................................ 424/725, 777; 426/599

(56) References Cited

U.S. PATENT DOCUMENTS

6,159,512 A * 12/2000 Reyes

FOREIGN PATENT DOCUMENTS

| JP | 8208501 | * | 8/1996 |
| JP | 9110688 | * | 4/1997 |

OTHER PUBLICATIONS www.mangoxan.com website reference titled "You've Just Discovered MangoXan(TM)!" Downloaded (plus linker pages) in Apr. 2003 to Word Document (enclosed), 13 pages.*
www.larsoncenturyranch.com/Health website reference titled "The Origins of XanGo: Southeast Asia". Downloaded (plus linker pages) in Apr. 2003 to Word Document, 3 pages.*
Nakatani et al., *Inhibition of cyclooxygenase and prostaglandin $E_2$ synthesis by γ–mangostin, a xanthone derivative in mangosteen, in C6 rat glioma cells*, 63 Biochemical Pharmacology, pp. 73–79 (2002).
Yaacob et al., *Mangosteen cultivation*, Plant Production and Protection Paper, pp. 10–13 (Food and Agriculture Organization of the United Nations) (1995).
Duke et al., *CRC Handbook of Alternative Cash Crops*, pp. 257–259 (CRC Press) (1993).
Dahanukar et al., *Pharmacology of medicinal plants and natural products*, Indian Journal of Pharmacology, p. S96 (2000).
*Thai Medicinal Plants—Recommended for Primary Health Care System*, pp. 160–162 (Norman Farnsworth ed., Medicinal Plant Information Center, Thailand) (1992).

Jinsart et al., *Inhibition of wheat embryo calcium–dependent protein kinase and other kinases by mangostin and γ–mangostin*, 31 Phytochemistry No. 11, pp. 3711–3713 (1992).
Kirtikar et al., *Indian Medicinal Plants*, pp. 261–262 (International Book Distributors, India) (2d ed. 1999).
J.F. Caius, *The Medicinal and Poisonous Plants of India*, pp. 430–431 (Scientific Publishers, India) (1986).
Du et al., *A Research Note—Anthocyanins of mangosteen, Garcinia mangostana*, 42 Journal of Food Science No. 6, pp. 1667–1668 (1977).
Shankaranarayan et al., *Pharmacological Profile of Mangostin and Its Derivatives*, 239 int. Pharmacodyn, pp. 257–269 (India) (1979).
Shankaranarayanan et al., *Effects of Mangostin, a Xanthone from Garcinia mangostana Linn, in Immunopathological and Inflammation Reactions*, 18 Indian Journal of Experimental Biology, pp. 843–846 (1980).
Chairungsrilerd et al., *Mangostanol, A Prenyl Xanthone from Garcinia mangostana*, 43 Phytochemistry No. 5, pp. 1099–1102 (1996).
Mahabusarakam et al., *Antimicrobial Activities of Chemical Constituents from Garcinia mangostana Linn.*, 12 J. Sci. Soc. Thailand, pp. 239–242 (1986).
Chairungsrilerd et al., *Histaminiergic and Serotonergic Receptor Blocking Substances from the Medicinal Plant Garcinia mangostana*, 62 Planta Medica, pp. 471–472 (1996).
Chen et al., *Active Constituents Against HIV–1 Protease from Garcinia mangostana*, 62 Planta Medica, pp. 381–382 (1996).
Mahabusarakam et al., *Inhibition of Lipoprotein Oxidation by Prenylated Xanthones Derived from Mangostin*, 33 Free Rad. Res., pp. 643–659 (2000).
"www.foodmarketexchange.com" web page showing 'Mangosteen wine ready to make debut', downloaded from Internet on Aug. 12, 2003.
"www.mistic.com" web page showing 'Mistic Zotics—Thailand Mangosteen Fruit', downloaded from Internet on Nov. 9, 2002.

\* cited by examiner

*Primary Examiner*—Christopher R. Tate
(74) *Attorney, Agent, or Firm*—Stephen H. Bean

(57) ABSTRACT

Nutraceutical compositions derived from the fruit of the *Garcinia mangostana* L. or mangosteen plant are provided. The nutraceutical mangosteen compositions employ novel combinations of mangosteen fruit pulp and pericarp, and can be additionally complemented by selected juice concentrates to yield a composition for improving general health and wellness in humans.

81 Claims, No Drawings

NUTRACEUTICAL MANGOSTEEN COMPOSITION

BACKGROUND OF THE INVENTION

1. Field of the Invention

The present invention relates to nutraceutical compositions derived from the fruit of the *Garcinia mangostana L.* plant, otherwise known as the mangosteen plant. More particularly, the present invention relates to nutraceutical compositions comprising a mixture of the pulp and pericarp of the mangosteen fruit.

2. Background and Related Art

The mangosteen tree (*Garcinia mangostana L.*) was named after the French explorer Laurent Garcin (1683–1751) and has been cultivated for a considerable time in tropical areas of the world. The tree is presumed to have originated in South-east Asia or Indonesia and has largely remained indigenous to the Malay Peninsula, Myanmar, Thailand, Cambodia, Vietnam, the Sunda Islands, and the Moluccas. Although the mangosteen fruit is highly praised as one of the best tasting of all tropical fruits, it is considered a minor tropical fruit, and the mangosteen tree has largely piqued purely botanical interests over the years.

The mangosteen tree is a slow-growing, smooth evergreen tree that ranges from 5 to 25 meters in height with a flaking black bark that contains a yellow, resinous latex. The mangosteen tree bears fruit when 6 to 20 years old, depending on location, and can continue to yield fruit for up to 100 years. The mangosteen fruit ripens to a dark reddish-violet to black-violet color and is normally smooth or marked with brownish scars. The pericarp, or rind, of the mangosteen fruit is thick, tough, and exudes a bitter yellowish resin. Only about 25 to 30% of the mangosteen fruit consists of the edible pulp or rind, with the remainder comprising the tough, bitter pericarp. Each mangosteen fruit usually varies in weight from 75 to 120 grams and normally contains 2 to 3 well-developed seeds.

Over the years, the mangosteen plant has been used in a number of different ways. The timber is used for cabinets, building materials, fencing and furniture. The pericarp, containing pectin, tannins, resins and a yellow latex, is used in tanning and dyeing leather black. The fruit pulp is mostly used as a dessert, but can also be canned or made into preserves. However, when removing the fruit pulp from the rind, care must be taken to prevent the tannins and resins of the cut pericarp from contacting the fruit pulp. The mangosteen rind, leaves and bark have also been used as ingredients in folk medicine in areas where the plant grows indigenously. The thick mangosteen rind is used for treating catarrh, cystitis, diarrhea, dysentery, eczema, fever, intestinal ailments, itch, and skin ailments. The mangosteen leaves are used by some natives in teas and other decoctions for diarrhea, dysentery, fever, and thrush. It is also known that concoctions of mangosteen bark can be used for genitourinary afflictions and stomatosis.

Some of the medicinal properties of the *Garcinia mangostana L.* plant have been the subject of pharmacological and clinical studies. These studies have isolated chemical constituents in the mangosteen leaves, wood, pericarp and seed aril, which were found to contain the following biologically active compounds, among others: 1,6-dihydroxy-3-methoxy-2-(3-methyl-2-butenyl) xanthone, 1,5,8-trihydroxy-3-methoxy-2-(3-methyl-2-butenyl) xanthone, maclurin, 1,3,6,7-tetrahydroxy xanthone, 1,3,6,7-tetrahydroxy xanthone-O-β-D-glucoside, chrysanthemin, cyaniding-3-O-β-D-sophoroside, 8-deoxygartanin, 1,5-dihydroxy-2-isopentenyl-3-methoxy xanthone, 1,7-dihydroxy-2-isopentenyl-3-methoxy xanthone, 5,9-dihydroxy-8-methoxy-2,2-dimethyl-7-(3-methylbut-2-enyl) 2(H), 6(H)-pyrano-(3,2,6)-xanthen-6-one, fructose, garcinone A,B,C, D and E, gartanin, glucose, cis-hex-3-enyl acetate, 3-isomangostin, 3-isomangostin hydrate, 1-isomangostin, 1-isomangostin hydrate, kolanone, mangostin, β-mangostin, α-mangostin, mangostin-3,6-di-O-gulcoside, normangostin, sucrose, tannins, BR-xanthone-A, BR-xanthone-B, calabaxanthone demethylcalabaxanthone, 2-(γ,γ-dimethylallyl)-1,7-dihydroxy-3-methoxyxanthone, 2,8-bis-(γ,γ-dimethylallyl)-1,3,7-trihydroxyxanthone, 1,3,5, 8-tetrahydroxy-2,4-diprenylxanthone, and mangostanol. Many of these chemical constituents are xanthones, which are biologically active compounds that are receiving increasing interest in pharmacological studies for a variety of health benefits.

However, despite the pharmacological benefits of individual xanthone compounds and the native medicinal uses of the bark, leaves and rind of the mangosteen plant in South-east Asia and Indonesia, a nutraceutical composition containing the holistic benefits of the entire mangosteen fruit, including the fruit pulp and pericarp, is not known. In fact, it is recognized that when preparing the fruit pulp for consumption, care should be taken to separate from the delicious inner fruit pulp the outer pericarp with its resins and tannins, which are traditionally used to treat and stain leathers.

There exists a need in the nutritional arts for a nutraceutical composition that offers the health benefits of the entire mangosteen fruit, including the pulp and the pericarp. There also exists a need for a nutraceutical composition rich in natural xanthones for treating a variety of human ailments and conditions in an efficacious manner. Further, there is a need in the art for a natural xanthone product that is economical to manufacture.

SUMMARY OF THE INVENTION

The present invention relates to nutraceutical compositions derived from the fruit of the *Garcinia mangostana L.*, or mangosteen plant. More particularly, the present invention relates to efficacious nutraceutical compositions rich in natural xanthones that include the pulp and the pericarp of the mangosteen fruit. These compositions preferably comprise a mixture of mangosteen fruit pulp and pericarp with selected juice concentrates. In addition, the present invention relates to methods of preparing nutraceutical compositions of *Garcinia mangostana L.* plant that yield efficacious health supplements rich in natural xanthones. Further, the methods of preparing the mangosteen nutraceutical compositions are economical to operate.

A primary object of the present invention is to provide a nutraceutical composition that contributes to general human wellness and good health through a novel mixture of the pericarp and pulp of the fruit of the *Garcinia mangostana L.* plant. The effectiveness of this mixture is heightened through the addition of selected juice concentrates in varying amounts.

Another object of the present invention is to provide a nutraceutical composition that offers the holistic benefits of the entire mangosteen fruit and is an efficacious source of natural xanthone compounds.

An additional object of the present invention is to provide an antimicrobial and anti-inflammatory composition containing a therapeutic amount of natural xanthones derived from the *Garcinia mangostana L.* plant.

A further object of the present invention is to provide a xanthone-rich natural product with antioxidative properties.

Another object of the present invention is to provide a nutraceutical composition of *Garcinia mangostana L.* plant with beneficial antibacterial action.

An additional object of the present invention is to provide a process for preparing nutraceutical compositions of the *Garcinia mangostana L.* plant yielding the holistic benefits of the unique combination of mangosteen fruit pulp and pericarp, either alone or with complementary and enhancing juice concentrates.

Yet another object of the present invention is to provide an economical process for manufacturing nutraceutical compositions of the entire fruit of the *Garcinia mangostana L.* plant.

The foregoing and other objects, advantages and characterizing features will become apparent from the following description of certain illustrative embodiments of the invention.

While the methods and processes of the present invention have proven to be particularly useful in the area of nutritional health supplements, those skilled in the art can appreciate that the methods and processes can be used in a variety of different applications and in a variety of different areas of manufacture to satisfy a wide-ranging variety of pharmaceutical and medicinal needs.

The above-described features and advantages of the present invention, as well as additional features and advantages, will be set forth or will become more fully apparent in the description that follows and in the appended claims. The novel features which are considered characteristic of this invention are set forth in the attached claims. Furthermore, the features and advantages of the invention may be learned by the practice of the invention, or will be obvious to one skilled in the art from the description, as set forth hereinafter.

DETAILED DESCRIPTION OF THE INVENTION

The present invention relates to nutraceutical compositions derived from the *Garcinia mangostana L.* plant, otherwise known as the mangosteen plant. In particular, the compositions of the invention described herein uniquely provide natural xanthone compounds through the combination of the pulp and pericarp of the mangosteen fruit, along with selected juice and other phytochemical ingredients. The invention also relates to processes for manufacturing the nutraceutical compositions described herein in an economical manner.

It is understood that the terminology used herein is used for the purpose of describing particular embodiments only, and is not intended to limit the scope of the present invention. It is also understood that, as used herein and in the appended claims, the singular forms "a," "an," and "the" include plural reference, unless the context clearly dictates otherwise. In the disclosure and in the claims, the term "nutraceutical" shall refer to "any compounds or chemicals that can provide dietary or health benefits when consumed by humans or animals."

Unless defined otherwise, all technical and scientific terms used herein have the same meanings as commonly understood by one of ordinary skill in the art to which this invention belongs. Preferred methods, compositions, and materials of the present invention are described herein, although any methods and materials similar or equivalent to those described herein can by used in the practice or testing of the present invention. All references cited herein are incorporated by reference in their entirety.

The *Garcinia mangostana L.* plant, or mangosteen plant, is known for a variety of uses in the areas to which it is indigenous. For example, there are a number of folk medicines in South-east Asia and Indonesia that employ various decoctions of the leaves, root, and bark of the mangosteen plant, as well as of the pericarp of the mangosteen fruit. For example, according to the literature, the thick mangosteen pericarp can be used as an astringent or in various decoctions for treating catarrh, cystitis, diarrhea, dysentery, eczema, fever, intestinal ailments, itch, and skin ailments. Other medicinal uses of the leaves, root and bark would be known to one of skill in the art. Also, the outer pericarp of the mangosteen fruit, which contains pectins, tannins, resins and a yellow latex, is used for treating and staining leather black.

In contrast to the thick outer pericarp, the edible inner pulp of the mangosteen fruit is widely regarded for its exquisite taste. The inner pulp of a single mangosteen fruit usually consists of four to eight juicy, white-colored segments. When preparing the white pulp segments for consumption, care must be taken so as to not stain the pulp segments with the resins and tannins and other matter that oozes out of the cut outer pericarp. The need to keep the delicious white pulp separate from the dark purple, staining, bitter pericarp has long been known to those familiar with the mangosteen fruit.

Xanthones are biologically active plant phenols that naturally occur in a restricted group of plants. The general structure of a xanthone is:

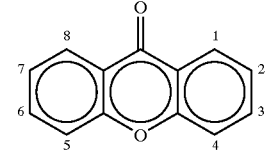

From a biosynthetic standpoint, they are related to the flavonoids, being formed by the condensation of a phenylpropanoid precursor with two instead of three malonyl coenzyme A units. Xanthones possess significant pharmacological properties, including antidepressant, antitubercular, antimicrobial, antiviral, anti-inflammatory, cardiotonic, antileukaemic, antitumor, antiulcer, antihepatotoxic, antiallergenic, and antirhinoviral activities and actions.

Pharmacological and botanical researchers have discovered that the medicinal properties of the mangosteen pericarp can be attributed to natural xanthones contained in the rind. The unrelated plant families Gentianaceae and Gutterferae are largely where naturally occurring hydroxanthones and their methyl ethers are found. The *Garcinia mangostana L.* plant, which contains a large number of naturally occurring xanthones, belongs within the Gutterferae family of plants.

Recent research has shown that the y-mangostin compound, a natural xanthone found in the *Garcinia mangostana L.* plant, inhibits type A and type B monoamine oxidases as well as cyclooxygenase and prostaglandin $E_2$ synthesis. (Nakatani et al., 63 Biochemical Pharmacology 73–79 (2002)). Under normal conditions in the brain, the levels of prostaglandin $E_2$ ($PGE_2$) are very low or even undetectable. However, during episodes of tissue inflammation, multiple sclerosis, and AIDS-related dementia, $PGE_2$ levels rise, and can affect the activities of neurons, glial, and endothelial cells. High levels of $PGE_2$ also affect microglia/macrophage and lymphocyte functions. It is widely understood that the generation of prostaglandins is associated with inflammation, pain and fever.

Cyclooxygenase is the rate-limiting enzyme in prostaglandin production. There are two isoforms of cyclooxygenase (COX), constitutive (COX-1) and inducible (COX-2), which is expressed in response to inflammation stimuli. The xanthone γ-mangostin is found to directly inhibit activity of both COX isoforms as well as $PGE_2$ synthesis, which makes this xanthone desirable in the treatment of inflammatory conditions as well as symptoms of fever and pain. The nutraceutical compositions of the present invention offer therapeutic amounts of important xanthones, including γ-mangostin, from a natural source to provide increased health and general wellness in humans.

In the present invention, it has been discovered that a mixture of the mangosteen pericarp and fruit pulp in a single nutraceutical composition yields surprising health benefits. The efficacy of this xanthone-rich mixture of mangosteen pericarp and pulp is enhanced through the addition of selected juice and phytochemical ingredients, which are believed to synergistically react with the natural xanthone compounds. In a preferred embodiment of the invention, the mixture of mangosteen fruit pulp and pericarp is complemented by the addition of one or more juice concentrates selected from the group consisting of alfalfa juice concentrate, apple juice concentrate, apricot juice concentrate, banana juice concentrate, blueberry juice concentrate, cantaloupe juice concentrate, carrot juice concentrate, celery juice concentrate, cherry juice concentrate, cranberry juice concentrate, grape juice concentrate, grapefruit juice concentrate, green barley juice concentrate, green lettuce juice concentrate, kale juice concentrate, kiwi fruit juice concentrate, orange juice concentrate, papaya juice concentrate, parsley juice concentrate, pear juice concentrate, pear puree, pineapple juice concentrate, prune juice concentrate, raspberry juice concentrate, spinach juice concentrate, strawberry juice concentrate and tomato juice concentrate.

The nutraceutical compositions of the present invention deliver therapeutic amounts of natural xanthone compounds derived from the mangosteen fruit pulp and pericarp mixture. In one embodiment of the present invention, the mixture of mangosteen fruit pulp and pericarp is present in an amount ranging from between 3 and 50%, preferably between 5 and 25%, and most preferably between 10 and 20% of the total weight of mangosteen mixture and selected juice concentrates. In another embodiment of the invention, the nutraceutical composition comprising mangosteen fruit pulp and pericarp is formulated for oral administration. However, the present compositions can be delivered in any form known in the art, such as tablets, capsules, dispersions, solutions, suspensions, transdermal delivery systems, etc. If the mangosteen pericarp and fruit pulp mixture is complemented with selected juice concentrates, then a liquid beverage is a convenient delivery form, but other delivery forms are equally efficacious and would simply require the use of powders or other equivalent forms of the juice concentrates. Tablets or capsule forms of the present nutraceutical compositions can be prepared and coated by methods known to those of ordinary skill in the art. When the nutraceutical compositions of the present invention are presented in liquid beverage form, the ratio of water to mangosteen mixture and selected juice concentrates can be 1:1, preferably 3:1 and most preferably 4:1.

The nutraceutical compositions of the present invention can be produced through large-scale, economical operations. In one embodiment of the invented process, whole fruit from the *Garcinia mangostana L.* plant is picked and transported to a production facility. The fresh fruit can kept at ambient air temperatures during transportation or it can be frozen, depending on need. The entire mangosteen fruit, including the fruit pulp and pericarp, is then ground into a pulp and pericarp mixture using commercial grinding or mixing equipment. The resulting mixture of mangosteen fruit pulp and pericarp can then be further processed through the addition of one or more of the selected juice concentrates listed above. In preferred embodiments of the beverage form of the invention, the selected juice concentrates and water are then added to the mixture in accordance with the amounts, ranges and ratios specified above. The liquid nutraceutical compositions can then be treated, bottled or packaged for distribution to consumers using a variety of methods known to those of ordinary skill in the art, such as pasteurization, flash pasteurization, sterilization, UHT sterilization, pressure sealing, freezing, freeze drying, irradiating, etc. Dehydrated and other forms of the nutraceutical compositions can also be prepared using standard techniques.

The effectiveness in improving general health and wellness of the nutraceutical mangosteen compositions described herein is demonstrated from the following clinical examples, which are listed for illustrative purposes only and are not meant to be limiting instances of therapeutic use. A therapeutic composition of the mangosteen fruit pulp and pericarp mixture was prepared according to the embodiments described herein. Each subject ingested 3 ounces of the beverage daily for a three week period. The following qualitative results were obtained:

EXAMPLE 1

The subject was a 62-year-old female suffering from chronic back pain, nausea and chronic vertigo. Prior to the study, the pack pain was treated with oral doses of morphine three times a day. After a regiment of the mangosteen nutraceutical composition, the subject experienced improved energy, less nausea and a decrease in the vertigo symptoms.

EXAMPLE 2

The subject was a 56-year-old male suffering from chronic obstructive pulmonary disease, muscle aches, fatigue and dysthemia. After a regiment of the mangosteen nutraceutical composition, the subject experienced improvement in mood, energy and muscle aches in the shoulders and back.

EXAMPLE 3

The subject was a 55-year-old male suffering from irritable bowel syndrome. After a regiment of the mangosteen nutraceutical composition, the subject experienced regularization of bowel movements.

EXAMPLE 4

The subject was a 30-year-old male suffering from chronic neck pain, familial hyperlipidemia, fatigue and insomnia. After a regiment of the mangosteen nutraceutical composition, the subject experienced improved energy and a decrease in low-density lipoproteins.

EXAMPLE 5

The subject was a 52-year-old male suffering from hypokelemia, fatigue and weight gain. After a regiment of the mangosteen nutraceutical composition, the subject experienced improved energy and a normalization of potassium levels.

EXAMPLE 6

The subject was a 63-year-old female suffering from degenerative arthritis, C-difficile colitis, fatigue, decreased appetite hypokelemia, and numbness of the fingers and toes. After a regiment of the mangosteen nutraceutical composition, the subject experienced improvement in colitis, reduction of pain in wrists and hands and a normalization of potassium levels.

EXAMPLE 7

The subject was a 66-year-old male suffering from a severe allergy reaction causing desquamation of palms, fingers, soles of feet and the inside of the mouth and esophagus. After a regiment of the mangosteen nutraceutical composition, the subject was completely cured.

EXAMPLE 8

The subject was a 57-year-old male suffering from malaise, muscle aches, hepatitis, glomerionephritis, diabetes and hyperlipidemia. After a regiment of the mangosteen nutraceutical composition, the subject experienced a 30 point decrease in low-density lipoproteins, a 10 point increase in high-density lipoproteins, improved energy, a 14-pound weight loss and the malaise was eliminated.

EXAMPLE 9

The subject was a 30-year-old male suffering from a chronic dermal rash. After a regiment of the mangosteen nutraceutical composition, the rash was completely eliminated.

EXAMPLE 10

The subject was a 25-year-old female suffering from low energy levels. After a regiment of the mangosteen nutraceutical composition, the subject experienced increased energy.

EXAMPLE 11

The subject was a 28-year-old female suffering from extreme fatigue and depression. After a regiment of the mangosteen nutraceutical composition, the subject experienced a significant increase in energy.

EXAMPLE 12

The subject was a 26-year-old female suffering from irritable bowel syndrome. After a regiment of the mangosteen nutraceutical composition, the subject experienced a decrease in cramping and stool frequency and increased energy.

EXAMPLE 13

The subject was a 32-year-old male marathon runner and iron man competitor. After a regiment of the mangosteen nutraceutical composition, the subject experienced increased energy levels.

EXAMPLE 14

The subject was a 70-year-old female suffering from severe arthritis. After a regiment of the mangosteen nutraceutical composition, the subject experienced complete elimination of arthritic symptoms and increased energy.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A nutraceutical beverage comprising:
   pericarp from fruit of a *Garcinia mangostana L.* tree;
   a first juice from fruit of a *Garcinia mangostana L.* tree; and
   at least one second juice selected from the group consisting of fruit juice and vegetable juice.

2. The nutraceutical beverage of claim 1, wherein said at least one second juice comprises fruit juice.

3. The nutraceutical beverage of claim 2, wherein said fruit juice is comprised of at least one of apple juice, apricot juice, banana juice, blueberry juice, cantaloupe juice, cherry juice, cranberry juice, grape juice, grapefruit juice, kiwi fruit juice, orange juice, papaya juice, pear juice, pear puree, pineapple juice, prune juice, raspberry juice and strawberry juice.

4. The nutraceutical beverage of claim 1, wherein said at least one second juice comprises vegetable juice.

5. The nutraceutical beverage of claim 4, wherein said vegetable juice is comprised of at least one of alfalfa juice, carrot juice, celery juice, green barley juice, green lettuce juice, kale juice, parsley juice, spinach juice and tomato juice.

6. The nutraceutical beverage of claim 1, wherein said pericarp from fruit of a *Garcinia mangostana L.* tree is processed from whole fruit pericarp.

7. The nutraceutical beverage of claim 6, wherein said pericarp comprises ground pericarp.

8. The nutraceutical beverage of claim 6, wherein said pericarp comprises powdered pericarp.

9. The nutraceutical beverage of claim 2 and claim 3, wherein said fruit juice comprises juice from concentrate.

10. The nutraceutical beverage of claim 4 and claim 5, wherein said vegetable juice comprises juice from concentrate.

11. The nutraceutical beverage of claim 1, wherein said juice comprises juice from concentrate.

12. The nutraceutical beverage of claim 11, wherein said juice from concentrate is comprised of at least one of apple juice, blueberry juice, cherry juice, cranberry juice, grape juice, pear juice, pear puree, raspberry juice and strawberry juice.

13. The nutraceutical beverage of claim 11, wherein said juice from concentrate is comprised of at least one of blueberry juice, cherry juice, cranberry juice, grape juice and pear juice.

14. The nutraceutical beverage of claim 6, claim 7 and claim 8 wherein said second juice is comprised of juice from concentrate.

15. The nutraceutical beverage of claim 11, wherein a percentage by weight of said pericarp from fruit of a *Garcinia mangostana L.* tree and said juice from fruit of a *Garcinia mangostana L.* tree is approximately 3% to 50% of a total weight of said pericarp from fruit of a *Garcinia mangostana L.* tree, said juice from fruit of a *Garcinia mangostana L.* tree and said juice from concentrate.

16. The nutraceutical beverage of claim 11, wherein a percentage by weight of said pericarp from fruit of a *Garcinia mangostana L.* tree and said juice from fruit of a

*Garcinia mangostana L.* tree is approximately 5% to 25% of a total weight of said pericarp from fruit of a *Garcinia mangostana L.* tree, said juice from fruit of a *Garcinia mangostana L.* tree and said juice from concentrate.

17. The nutraceutical beverage of claim 11, wherein a percentage by weight of said pericarp from fruit of a *Garcinia mangostana L.* tree and said juice from fruit of a *Garcinia mangostana L.* tree is approximately 10% to 20% of a total weight of said pericarp from fruit of a *Garcinia mangostana L.* tree, said juice from fruit of a *Garcinia mangostana L.* tree and said juice from concentrate.

18. The nutraceutical beverage of claim 11, wherein a ratio of water to said pericarp from fruit of a *Garcinia mangostana L.* tree, said juice from fruit of a *Garcinia mangostana L.* tree and said juice from concentrate is approximately 1:1.

19. The nutraceutical beverage of claim 11, wherein a ratio of water to said pericarp from fruit of a *Garcinia mangostana L.* tree, said juice from fruit of a *Garcinia mangostana L.* tree and said juice from concentrate is approximately 3:1.

20. The nutraceutical beverage of claim 11, wherein a ratio of water to said pericarp from fruit of a *Garcinia mangostana L.* tree, said juice from fruit of a *Garcinia mangostana L.* tree and said juice from concentrate is approximately 4:1.

21. A nutraceutical beverage comprising:
pericarp from fruit of a *Garcinia mangostana L.* tree;
a first juice from fruit of a *Garcinia mangostana L.* tree; and
a second juice, comprising at least one of apple juice; blueberry juice; cherry juice; cranberry juice; grape juice; pear juice; pear puree; raspberry juice; and strawberry juice.

22. The nutraceutical beverage of claim 21, wherein said second juice comprises juice from concentrate.

23. The nutraceutical beverage of claim 22, wherein a percentage by weight of said pericarp and said first is approximately 3% to 50% of a total weight of said pericarp, said first juice and said second juice.

24. The nutraceutical beverage of claim 22, wherein a percentage by weight of said pericarp and said first is approximately 5% to 25% of a total weight of said pericarp, said first juice and said second juice.

25. The nutraceutical beverage of claim 22, wherein a percentage by weight of said pericarp and said first is approximately 10% to 20% of a total weight of said pericarp, said first juice and said second juice.

26. The nutraceutical beverage of claim 22, wherein a ratio of water to said pericarp, said first juice and said second juice is approximately 1:1.

27. The nutraceutical beverage of claim 22, wherein a ratio of water to said pericarp, said first juice and said second juice is approximately 3:1.

28. The nutraceutical beverage of claim 22, wherein a ratio of water to said pericarp, said first juice and said second juice is approximately 4:1.

29. A nutraceutical composition, comprising:
pericarp from fruit of a *Garcinia mangostana L.* tree; and
at least one fruit or vegetable juice other than mangosteen juice combined with said pericarp into a nutraceutical composition.

30. The nutraceutical composition of claim 29, wherein said at least one juice comprises fruit juice.

31. The nutraceutical composition of claim 30, wherein said fruit juice is comprised of at least one of apple juice, blueberry juice, cherry juice, cranberry juice, grape juice, pear juice, pear puree, raspberry juice and strawberry juice.

32. The nutraceutical composition of claim 29, wherein said at least one juice comprises vegetable juice.

33. The nutraceutical composition of claim 32, wherein said vegetable juice is comprised of at least one of alfalfa juice, carrot juice, celery juice, green barley juice, green lettuce juice, kale juice, parsley juice, spinach juice and tomato juice.

34. The nutraceutical composition of claim 29, further comprising processed fruit pulp from fruit of a *Garcinia mangostana L.* tree.

35. The nutraceutical composition of claim 29, wherein said at least one juice comprises juice from concentrate.

36. The nutraceutical composition of claim 29, wherein said at least one juice comprises a juice powder.

37. The nutraceutical composition of claim 29, wherein said nutraceutical composition comprises a syrup.

38. The nutraceutical composition of claim 29, wherein said nutraceutical composition comprises a powdered drink mix.

39. The nutraceutical composition of claim 29, wherein said nutraceutical composition comprises a tablet.

40. The nutraceutical composition of claim 29, wherein said nutraceutical composition comprises a capsule.

41. The nutraceutical composition of claim 29, wherein the percentage by weight of said pericarp and said juice is approximately 3% to 50% of the total weight of said nutraceutical composition.

42. The nutraceutical composition of claim 29, wherein the percentage by weight of said pericarp and said juice is approximately 5% to 25% of the total weight of said nutraceutical composition.

43. The nutraceutical composition of claim 29, wherein the percentage by weight of said pericarp and said juice is approximately 10% to 20% of the total weight of said nutraceutical composition.

44. A nutraceutical beverage comprising:
processing fruit of a *Garcinia mangostana L.* tree;
processing pericarp from fruit of a *Garcinia mangostana L.* tree;
providing at least one fruit or vegetable juice other than mangosteen juice; and
combining said processed fruit pulp, said processed pericarp and said at least one fruit or vegetable juice into a mixture.

45. The method of claim 44, wherein said providing comprises providing fruit juice.

46. The method of claim 45, wherein said providing comprises providing at least one of apple juice, apricot juice, banana juice, blueberry juice, cantaloupe juice, cherry juice, cranberry juice, grape juice, grapefruit juice, kiwi fruit juice, orange juice, papaya juice, pear juice, pear puree, pineapple juice, prune juice, raspberry juice and strawberry juice.

47. The method of claim 44, wherein said providing comprises providing vegetable juice.

48. The method of claim 47, wherein said providing comprises providing at least one of alfalfa juice, carrot juice, celery juice, green barley juice, green lettuce juice, kale juice, parsley juice, spinach juice and tomato juice.

49. The method of claim 44, further comprising flash pasteurizing said mixture.

50. The method of claim 44, wherein said providing comprises providing a fruit or vegetable concentrate.

51. The method of claim 50, further comprising providing a percentage by weight of said processed fruit pulp and said processed pericarp in an amount of approximately 3% to 50% of the total weight of said processed fruit pulp, said processed pericarp and said juice concentrate.

52. The method of claim 50, further comprising providing a percentage by weight of said processed fruit pulp and said processed pericarp in an amount of approximately 5% to 25% of the total weight of said processed fruit pulp, said processed pericarp and said juice concentrate.

53. The method of claim 50, further comprising providing a percentage by weight of said processed fruit pulp and said processed pericarp in an amount of approximately 10% to 20% of the total weight of said processed fruit pulp, said processed pericarp and said juice concentrate.

54. The method of claim 50, further comprising providing a ratio of water to said processed fruit pulp, said processed pericarp and said juice concentrate of approximately 1:1.

55. The method of claim 50, further comprising providing a ratio of water to said processed fruit pulp, said processed pericarp and said juice concentrate of approximately 3:1.

56. The method of claim 50, further comprising providing a ratio of water to said processed fruit pulp, said processed pericarp and said juice concentrate of approximately 4:1.

57. The method of claim 44, further comprising forming said mixture into a syrup.

58. The method of claim 44, further comprising forming said mixture into a powdered drink mix.

59. The method of claim 44, further comprising forming said mixture into a tablet.

60. The method of claim 44, further comprising forming said mixture into a capsule.

61. The method of claim 44, further comprising forming said mixture into a beverage.

62. A method of preparing a nutraceutical composition, comprising:
grinding fruit from a *Garcinia mangostana L.* tree;
grinding pericarp from a *Garcinia mangostana L.* tree;
providing at least one juice concentrate other than mangosteen juice concentrate; and
combining said ground fruit pulp, said ground pericarp and said at least one juice concentrate other than mangosteen juice concentrate into a mixture.

63. The method of claim 62, wherein said providing comprises providing fruit juice concentrate.

64. The method of claim 63, wherein said providing comprises providing at least one of apple juice concentrate, apricot juice concentrate, banana juice concentrate, blueberry juice concentrate, cantaloupe juice concentrate, cherry juice concentrate, cranberry juice concentrate, grape juice concentrate, grapefruit juice concentrate, kiwi fruit juice concentrate, orange juice concentrate, papaya juice concentrate, pear juice concentrate, pear puree concentrate, pineapple juice concentrate, prune juice concentrate, raspberry juice concentrate and strawberry juice concentrate.

65. The method of claim 62, wherein said providing comprises providing vegetable juice concentrate.

66. The method of claim 65, wherein said providing comprises providing at least one of alfalfa juice concentrate, carrot juice concentrate, celery juice concentrate, green barley juice concentrate, green lettuce juice concentrate, kale juice concentrate, parsley juice concentrate, spinach juice concentrate and tomato juice concentrate.

67. The method of claim 62, further comprising providing a percentage by weight of said ground fruit pulp and said ground pericarp in an amount of approximately 3 to 50% of said mixture.

68. The method of claim 62, further comprising providing a percentage by weight of said ground fruit pulp and said pericarp in an amount of approximately 5 to 25% of said mixture.

69. The method of claim 62, further comprising providing a percentage by weight of said ground fruit pulp and said ground pericarp in an amount of approximately 10 to 20% of said mixture.

70. The method of claim 62, further comprising providing a ratio of water to said ground fruit pulp, said ground pericarp and said at least one juice concentrate other than mangosteen juice concentrate of approximately 1:1.

71. The method of claim 62, further comprising providing a ratio of water to said ground fruit pulp, said ground pericarp and said at least one juice concentrate other than mangosteen juice concentrate of approximately 3:1.

72. The method of claim 62, further comprising providing a ratio of water to said ground fruit pulp, said ground pericarp and said at least one juice concentrate other than mangosteen juice concentrate of approximately 4:1.

73. A method for preparing a nutraceutical beverage, comprising:
grinding whole pericarp from a *Garcinia mangostana L.* tree for form ground whole pericarp;
providing at least one fruit or vegetable juice other than mangosteen juice;
mixing said ground whole pericarp with said at least one fruit or vegetable juice other than mangosteen juice to form a liquid pericarp mixture; and
bottling said liquid pericarp mixture.

74. The method of claim 73, further comprising pasteurizing said liquid pericarp mixture before said bottling step.

75. The method of claim 73, further comprising providing a ratio of water to said liquid pericarp mixture of approximately 1:1.

76. The method of claim 73, further comprising providing a ratio of water to said liquid pericarp mixture of approximately 3:1.

77. The method of claim 73, further comprising providing a ratio of water to said liquid pericarp mixture of approximately 4:1.

78. The method of claim 73, wherein said providing comprises providing fruit juice.

79. The method of claim 78, wherein said providing comprises providing at least one of apple juice, apricot juice, banana juice, blueberry juice, cantaloupe juice, cherry juice, cranberry juice, grape juice, kiwi fruit juice, orange juice, papaya juice, pear juice, pear puree, pineapple juice, prune juice, raspberry juice and strawberry juice.

80. The method of claim 73, wherein said providing comprises providing vegetable juice.

81. The method of claim 80, wherein said providing comprises providing at least one of alfalfa juice, carrot juice, celery juice, green barley juice, green lettuce juice, kale juice, parsley juice, spinach juice and tomato juice.

\* \* \* \* \*

UNITED STATES PATENT AND TRADEMARK OFFICE
CERTIFICATE OF CORRECTION

PATENT NO. : 6,730,333 B1
DATED : May 4, 2004
INVENTOR(S) : Aaron R. Garrity et al.

It is certified that error appears in the above-identified patent and that said Letters Patent is hereby corrected as shown below:

Column 1,
Line 36, change the term "edible pulp or rind" to -- edible pulp or aril --.
Line 54, delete the word "arc" and replace with the word -- are --.

Column 3,
Line 4, add the word -- the -- in front of "*Garcinia mangostana*" so the text reads -- nutraceutical composition of the *Garcinia mangostana* L. plant --.

Column 4,
Line 59, replace "y-mangostin" with -- γ-mangostin --.

Column 8,
Lines 44-45, insert the word -- second -- so the text reads "wherein said second juice".

Column 9,
Lines 39, 43 and 47, insert the word -- juice -- so that the text reads " said first juice is".

Column 10,
Line 38, change the phrase "A nutraceutical beverage comprising" to -- A method of preparing a nutraceutical composition, comprising --.
Line 39, change the phrase "processing fruit of" to -- processing fruit pulp from --.
Lines 40-41, change the phrase "pericarp from fruit of a *Garcinia mangostana* L. tree" to -- pericarp from a *Garcinia mangostana* L. tree --.

Column 11,
Line 1, delete the word "the" and replace with -- a -- so that the text reads "50% of a total weight".
Line 34, insert the word -- pulp -- so that the text reads "grinding fruit pulp from".

UNITED STATES PATENT AND TRADEMARK OFFICE
CERTIFICATE OF CORRECTION

PATENT NO. : 6,730,333 B1
DATED : May 4, 2004
INVENTOR(S) : Aaron R. Garrity et al.

It is certified that error appears in the above-identified patent and that said Letters Patent is hereby corrected as shown below:

<u>Column 12,</u>
Lines 6-7, insert the word -- ground -- so that the text reads "said ground pericarp".
Line 28, change the phrase "tree for form" to -- tree to form --.
Line 51, insert the words -- grapejuice-- so that the text reads "grape juice, grape-fruit juice, kiwi fruit juice".

Signed and Sealed this

Seventeenth Day of May, 2005

JON W. DUDAS
*Director of the United States Patent and Trademark Office*

US006730333C1

(12) EX PARTE REEXAMINATION CERTIFICATE (7319th)

United States Patent
Garrity et al.

(10) Number: US 6,730,333 C1
(45) Certificate Issued: Jan. 12, 2010

(54) NUTRACEUTICAL MANGOSTEEN COMPOSITION

(75) Inventors: Aaron R. Garrity, Pleasant Grove, UT (US); Gordon A. Morton, Springville, UT (US); Joseph C. Morton, Springville, UT (US)

(73) Assignee: DBC, LLC, Orem, UT (US)

Reexamination Request:
No. 90/007,178, Aug. 20, 2004

Reexamination Certificate for:
Patent No.: 6,730,333
Issued: May 4, 2004
Appl. No.: 10/283,600
Filed: Oct. 30, 2002

Certificate of Correction issued May 17, 2005.

(51) Int. Cl.
*A61K 36/00* (2006.01)
*A23L 2/00* (2006.01)

(52) U.S. Cl. .................. 424/777; 424/725; 426/599
(58) Field of Classification Search .................. 424/725
See application file for complete search history.

(56) References Cited

U.S. PATENT DOCUMENTS

| | | | |
|---|---|---|---|
| 4,592,913 A | 6/1986 | Hara | |
| 5,554,286 A | 9/1996 | Okamoto et al. | |
| 6,177,096 B1 | 1/2001 | Zerbe et al. | |
| 6,231,866 B1 | 5/2001 | Mann | |
| 6,419,903 B1 | 7/2002 | Xu et al. | |
| 6,455,057 B1 | 9/2002 | Barrett et al. | |
| 6,596,298 B2 | 7/2003 | Leung et al. | |
| 2003/0138467 A1 | 7/2003 | Ptchelintsev | |
| 2003/0206942 A1 | 11/2003 | Kulkami et al. | |

FOREIGN PATENT DOCUMENTS

| | | | |
|---|---|---|---|
| EP | 00496349 A1 | | 7/1992 |
| JP | 02009817 | | 1/1990 |
| JP | 8-208501 | | 8/1996 |
| JP | 08208501 | * | 8/1996 |
| JP | 09110688 | | 4/1997 |
| JP | 9-110688 | | 4/1997 |
| JP | 11-43442 | | 2/1999 |
| JP | 11043442 | * | 2/1999 |
| JP | 2001247469 A | | 11/2001 |

OTHER PUBLICATIONS

Edited by Philip Ashurst, Aspen Publication, Food Flavorings, Third edition, 1999, pp. 407–421.*
"www.foodmarketexchange.com" web page showing 'Mangosteen wine ready to make debut'.
"www.mistic.com" web page showing 'Mistic Zotics—Thailand Mangosteen Fruit'.
Chanarat P., et al., ImmunopharmacologicalActivity of Polysaaccharide from the Pericarp of Mangosteen Garcinia: Phagocytic Intracellular Killing Activities, 80 Supp. 1 J. Med. Assoc. Thai., S149–54 (Sep. 1997).
Duke et al., CRC Handbook of Alternative Cash Crops, 257–59,474–98 (1993).
Furukawa K, et al., Novel Types of Receptor Antagonist from the Medicinal Plant Garcinia Mangostans, Nippon Yakurigaku Zasshi, 110 Supp.1: 153–1158 (Feb. 1998).
Furukawa K., et al., The Mode of Inhibitory Action of Alpha–Mangostin, a Novel Inhibitor, on the Sarcoplasmic Reticulum Ca (2+)–Pumping ATPase from Rabbit Skeletal Muscle, 71(4) Jpn. J. Pharmacol., 337–40 (Aug. 1996).
Iinuma M, et al., Antibacterial Activity of Xanthones from Guttiferaeous Plants Against Methicillin–Resistant Staphylococcus aureus, 48(8) J. Pharm. Pharmacol. 861–5 (Aug. 1996).
Settheetham W., and Ishida T., Study of Genotoxic Effects of Antidiarrheal Medicinal Herbs on Human Cells in Vitro, Southeast Asian J. Trop Med Public Health., 26 Supp. 1:306–310 (1995).
Siddappa and Bhatie, Preservation of Mangosteen (*Garcinia mangostana* L.), Bull. Centr. Food Res. Inst. Mysore, India 3: 296–97 (1954).
Nattaya Chairugsrilerd, et al., Mangostanol, a Prenyl Xanthone From *Garcinia Mangostana*, Photochemistry, vol. 43, No. 5, pp. 1099–1102 (1996).
J.F. Caius, The Medicinal and Poisonous Plants of India (1986).
Wanida Jinsart, et al., Inhibition of Wheat Embryo Calcium–Dependent Protein Kinase and other Kinanses by Mangostin, Phytochemistry, vol. 31, No. 11, pp. 3711–3713 (1992).
K.R. Kirtikar, et al., Indian Medicinal Plants 261–62 (1999).
Medical Plant Information Center, Thai Medicinal Plants 160–62(1992).
Keigo Nakatani et al., Inhibition of Cyclooxygenase and Prostaglandins E2 Synthesis By Mangostin, a Xanthone Derivative in Mangosteen, in C6 Rat Glioma Cells, 63 Biochemical Pharmacology 73–79 (2002).
D. ShanKaranarayan, et al., Pharmacological Profiles of Mangostin AndIits Derivatives, Pharmacodyn 257–69 (1979).
D. ShanKaranarayan, et al., Effect of Mangostin, a Xanthone from *Garcinia mangostana* Linn. In Immunopathological& Inflammatory Reactions, Indian Journal of Experimental Biology, vol. 18, Aug. 1980, pp. 843–846.

(Continued)

*Primary Examiner*—Michael V Meller

(57) ABSTRACT

Nutraceutical compositions derived from the fruit of the *Garcinia mangostana* L. or mangosteen plant are provided. The nutraceutical mangosteen compositions employ novel combinations of mangosteen fruit pulp and pericarp, and can be additionally complemented by selected juice concentrates to yield a composition for improving general health and wellness in humans.

At the time of issuance and publication of the certificate, the patent remains subject to pending reexamination control number 95/000,157 filed Sep. 13, 2006. The claim content of the patent may be subsequently revised if a reexaminaton certificate issues from the reexamination proceeding.

OTHER PUBLICATIONS

Yaacob et al., Mangosteen cultivation (1995).

Alternative Styles, Jun. 1, 2001, pp. 1–5, Beverage Industry Communications, Inc., ISSN: 0148–6187, vol. 92, Issue 6, 2001 WL 14821362.

Campbell, R.J., South American Fruits Deserving Further Attention, 1996, p. 431–439, In: J. Janick (ed.), Progress in new crops. ASHS Press, Arlington, VA.

Chairungsrilerd, Nattaya, et al., y–Mangostin, a Novel Type of 5–Hydroxytryptamine 2A Receptor Antagonist, Nauynym–Schmiedeberg's Arch Pharmacol, 1998, 357:25–31.

Chairungsrilerd, Nattaya, et al., Effect of y–mangostin through the inhibition of 5–hydroxy–tryptamine$_{2A}$ receptors in 5–fluoro–x–methyltryptamine–induced head–twitch response of mice, British Journal of Pharmacology, 1998, 123, 856–862.

Chen, M., Fruity Way to Good Health, Oct. 1, 2000, 3 pages, Sunday Mail, Malaysia, 2000 WL 2959378.

Clusiacaea, *Calophyllum inophyllum*L., pp. 214–218.

Dictionary entry for "*Garcinia cambogia*", p. 327.

Dictionary or Encyclopedia entry for "*Garcinia* L. Gulliferae", p. 1050.

Fairchild, D., The Mangosteen, The Journal of Heredity, pp. 339–347.

Frankfurt and Leipzig, Garcinia, Mangostan Tree, Botanical Encyclopedia, 1773, 3 pages, Fourth Edition.

Garcin, Laurentius, The Settling of a new Genus of Plans, called after the Malayans, Mangostans, Translated from the French by Mr. Zollman, F.R.S.

*Garcinia Mangostana* Linn: Mangostan, e–mail attachment, 1 page.

Gatorade Thirst Quencher—Sabor de Mangosteen, Sep. 6, 1999, 1 page, International Product Alert, ISSN: 1086–1238; vol. 16, Issue 17, 1999 WL 23229526.

Going to Extremes, Jul. 11, 1996, 2 pages, Gorman's New Product News, vol. 32, No. 6, ISSN: 1048–020X, 1996 WL 9833883.

Gopalakrishnan, G., et al., Evaluation of the Antifungal Activity of Natural Xanthones from *Garcinia Mangostana* and Their Synthetic Derivatives; J. Nat. Prod. 1997, 60, 519–524.

Greey, M, Vietnamese Give Drinks a Twist, Oct. 5, 1988, 3 pages, The Toronto Star, 1988 WL 5710363.

Hanes, P., Zesty Treats on Malaysian Streets Once Mainly Fish and Rice, Today's Fare Has a Mix of Flavors, Mostly from China and India, Oct. 24, 1991, 3 pages, Christian Science Monitor, 1991 WL 5363325.

Ho, C.K., Huang, Y.L., Chen, C.C., Garcinone E, a xanthone derivative, has potent cytotoxic effect against Hepatocellular carcinoma cell lines, 2 pages, Planta Med, 68(11): 975–79, 2002.

Holleran, J., The zotics Splash, Jun. 1, 2000, 7 pages, Beverage Industry, 2000 WL 18770402.

Hope, J., Mice Can Help Men to Become Fathers, Claims Fertility Doctor, 33/17/99, 2 pages, Daily Mail 6, 1999 WL 12913860.

Jardin, Kisantu, Le Jardin Botanique de Kisantu, printed from an e–mail on Aug. 3, 2004, 4 pages.

Kader, P., et al., Involvement of Blueberry Peroxidase in the Mechanisms of Anthocyanin Degradation in Blueberry Juice, Journal of Food Schience, 2002, vol. 67, No. 3, Institute of Food Technologists.

Likhitwitayawuld, K., et al., Antimalarial Xanthones from Garcinia Cowa, Planta Med. 1998, 64, 70–72.

Matsumoto, K., et al., Induction of Apoptosis by Xanthones from Mangosteen in Human Lukemia Cell Lines, J. Nat. Prod. 2003, 66, 1124–1127.

Mistic Zotics Beverage—Yuzu; Pitaya; Acerola Berry; Mangosteen; Marula, Apr. 24, 2000, 1 page, International Product Alert, ISSN: 0740–3801; vol. 30, Issue 8, 2000 WL 9202590.

Mokhtar N., Research to Diversify Use of Farm Products, Nov. 12, 1996, 3 pages, Business Times, Malaysia 02, 1996 WL 14216524.

Moongkarndi P, et al., Antiproliferation, Antioxidation and Induction of Apoptosis by *Gardinia Mangostant* (Mangosteen) on SKBR3 Human Breast Cancer Cell Line, J. Ethnopharmacol. Jan. 2004, 90(1):161–6, Pub Med search results, Department of Microbiology, Bangkok, Thailand.

Morton, J., Mangosteen, In: Fruits of Warm Climates, 1987, pp. 301–304, Miami, FL.

Morton, J. F., Major Medicinal Plants, Botany, Culture and Uses, 1977, pp. 1–12, Charles C. Thomas, Publisher, Springfield, Illinois.

Nakatani, Keigo, et al., Inhibitions of Histamine Release and Prostaglandin $E_2$ Synthesis by Mangosteen, A Thai Medicinal Plant, Biol. Pharm. Bull., Sep. 2002, 1137–1141, 25(9), Pharmaceutical Society of Japan.

New Products Blur the Lines, Mar. 1, 2001, pp. 1–4, Beverage Industry Communications, Inc., ISSN: 0148–6187, vol. 92, Issue 3, 2001 WL 14820975.

New Products Flavored with Orange, The Milwaukee Journal Sentinel, May 10, 2000, 2000 WL 3857627.

Okudaira, C., et al., Inhibition of Acidic Sphingomyelinase by Xanthone Compounds Isolated From Garcinia Speciosa, J. Enzyme Inhibition, 2000, vol. 15, pp. 129–138.

Paull, R.E., et al., Mangosteen, 3 pages, Department of Tropical Plant and Soil Sciences, University of Hawaii at Manoa, Honolulu, HI and Department of Horticulture, Kasetsart University, Bangkok, Thailand.

Perry, L. M., et al., Medicinal Plants of East and Southeast Asia, 5 pages and 174–175, 1980, The MIT Press, Cambridge, Massachusetts and London, England.

Plengmaneepun, S., Alcoholic Drinks: 'Grapes–Only' Rule Limits Opportunities, Aug. 13, 1999, 2 pages, Bangkok Post, 1999 WL 22710031.

Requested Recipe: Mangosteen Wine, The Winemaking Home Page, 2 pages, 2002.

Suksamrarn, S., et al., Xanthones from the Green Fruit Hulls of Garcinia Mangostana, Journal of Natural Products, 2002, pp. 761–63, vol. 65, No. 5, American Chemical Society and American Society of Pharmacognosy.

Sundaram, B.M., et al., Antimicrobial Activites of Garcinia Mangostana, Short Communications, pp. 59–60, 1983.

Sunkist Tropical Drink–13 Mangosteen, Nov. 3, 1997, 1 page, International Product Alert, vol. 14, No. 21 ISSN: 1086–1238, 1997 WL 12715299.

Sunkist World Fruits Puali Fruit Water—California Orange; Mediterranean Blend, Sep. 7, 1998, 1 page, International Product Alert, vol. 15, No. 17 ISSN: 1086–1238, 998 WL 14765678.

Templeman, J.F., Nuevo Suplemento Natural Impacta Comunidad Medica, La prensa Su Salad web site, printed from an e–mail on Aug. 3, 2004.

Toops, D., IFTA's Primary Theme—Wellness; But There Were Plenty of Surprises, Aug. 1, 2002, 6 pages, Food Processing Publishing Co., 2002 WL 14439138.

Torquay De–Lite Low Joule Natural Mineral Water—Apple, Plum & Blackcurrant; Lemon, Lime & Orange; Orange and Mangosteen; Peach and Cherimoya; Pink Grapefruit, Lemon & Mandarin, Nov. 6, 1999, 2 pages, International Product Alert, ISSN: 1086–1238; vol. 17, Issue 21, 1999 WL 31465706.

Torquay Reef Soft Drink—Lemon with a Hint of Raspberry; Lemonade with a Twist of Lime; Orange with a Splash of Mangsteen; Tropical with a Splice of Cherimoya and Passionfruit, Nov. 6, 1999, 2 pages, International Product Alert, ISSN: 1086–1238; vol. 17, Issue 21, 1999 WL 31465707.

Agroforestree Database, Garcinia Mangostana, pp. 1–6 printed from website on Aug. 3, 2004, World Agroforesty Centre.

Truly Top Quality, The Statesman—Asia Intelligence Wire, Apr. 19, 2001, 2001 WL 19354465.

Will Wellness Trend Live On? (Panel Discussion), Beverage Industry, Oct. 1, 2001, 2001 WL 29298168.

Williams, P., et al., Mangostin Inhibits the Oxidative Modification of Human Low Density Lipoprotein, Free Rad Res., vol. 23, No. 2, pp. 175–184, 1995, Harwood Academic Publishers GmBH, printed in Malaysia.

www.commercial–directory.com/diagnosispro/page1.htm, Toxicity Ratings for Herbals (From Planet–RX, PDR for Herbal Medicines, the AphA Practical Guide to Herbal Therapies, and H. Winter Griffith MD Guide and Many Other Sources, 2 pages.

www.hkbic.bch.cuhk.edu.hk/herbalLiteratureOnline/all–HerbalData.html, Record No. 67.

www.ibiblio.org/herbmed/eclectic/kings/garcinia–mang.html, King's American Dispensatory: Gardinia, printed from the Web on Apr. 29, 2002.

Chairungsrilerd, N, et al., Pharmacological Properties of α–mangostin, a Novel Histamine $H_1$ Receptor Antagonist, European Journal of Pharmacology, 314 (1996) pp. 351–356.

Civil Docket *Xango, LLC, et al v. New Vision USA, Inc., et al.*, U.S. District Court, District of Utah, Central Division, Case No. 2:04 CV00405 TC.

First Amended Complaint for Patent Infringement Jury Demanded, Jun. 8, 2004 (without Exhibit A).

Answer and Counterclaim on Behalf of Defendants to Plaintiffs' First Amended Complaint, Jun. 25, 2004 (with Exhibits 1–10).

Reply by Xango, LLC and DBC, LLC to Counterclaim by New Vision USA, Inc. Jul. 15, 2004.

Responses by Plaintiffs Xango, LLC and DBC, LLC to New Vision USA, Inc's First Set of Interrogatories (Nos. 1–9), Sep. 20, 2004.

Defendants' Responses to Plaintiffs Xango LLC and DBC LLC's First Set of Interrogatories, Sep. 20, 2004.

Defendants' Motion to Stay (with Exhibits A and F), Sep. 27, 2004.

Defendants' Supplemental Responses to Interrogatory Nos. 1, 2 and 5 Of Plaintiffs' First Set of Interrogatories, Oct. 11, 2004.

Supplemental Response by Plaintiffs Xango, LLC and DBC, LLC to New Vision USA Interrogatory No. 2, Oct. 11, 2004.

Plaintiffs' Memorandum in Opposition to Defendants' Motion to Stay (Filed Under Seal), Oct. 22, 2004.

Defendants' Reply Memorandum in Support of Defendants' Motion to Stay, Nov. 9, 2004.

Defendants' Supplemental Memorandum in Support of Motion to Stay (Filed Under Seal), Dec. 2, 2004.

Plaintiffs' Response Memorandum to Defendants' Supplemental Memorandum for Motion to Stay, Dec. 13, 2004.

Transcript of Proceedings, Motion to Stay, Dec. 15, 2004.

Plaintiffs' Claim Chart, Feb. 28, 2005.

Defendants' Second Supplemental Response to Interrogatory No. 5(A) Of Plaintiffs' First Set Of Interrogatories, Mar. 8, 2005.

Holleran, Joan, The Zotics Splash, Beverage Industry, Jun. 1, 2000, vol. 91, Issue 6, Information Access Company, WL 18770402.

Defendant's Second Supplemental Responses to Plaintiff's Interrogatories 1–10.

Bennett, Graham J. and Lee, Hiok–Huang, Review Article No. 43, Xanthones from Guttiferae, Phytochemistry, vol. 28, No. 4, pp. 967–998, 1989.

Peres, Valdir et al., Review, Tetraoxygenated Naturall Occurring Xanthones, Phytochemistry, vol. 55, pp. 683–710, 2000.

Maronia, H. et al., Pharmacological Properties of Some Aminoalkanolic Derivatives of Xanthone, Pharmazie, vol. 56, pp. 567–572, 2001.

Bates, R.P., et al., Principles and practices of small– and medium–scale fruit juice processing. FAO Agricultural Services Bulletin 146, Rome, 2001.

Letter (with attachments), dated May 23, 2005, from Edwin B. Wainscott of Quartes & Brady Streoch Lang LLP to Leland G. Hansen of McAndrews, Held & Malloy, Ltd.

Plaintiffs' Supplemental Claim Chart (with Exhibits 1–10), dated Mar. 18, 2005.

Plaintiffs' Addendum to Claim Chart, dated Mar. 29, 2005.

Defendants' Claim Chart, dated Apr. 4, 2005.

Plaintiffs' Claim construction Brief—Filed Under Seal, (with Exhibits A–C) (portions redacted), dated Mar. 18, 2005.

Plaintiffs' Claim Construction Evidence—vol. Two: Dictionaries, Treatises, and Other Evidence (Exhibits 44 and 45 redacted), dated Apr. 15, 2005.

Plaintiff's Presentation for Claim Construction Hearing—Apr. 21, 2005.

Defendants' Brief in Support of Claim Construction Definitions, dated Apr. 15, 2005.

Defendants' Motion to submit Corrected Claim Construction Brief, dated Apr. 20, 2005.

Joint Claim Construction Statement, dated Apr. 15, 2005.

Defendants' Response and Objections to Plaintiffs' Second Set of Interrogatories, dated Jan. 28, 2005.

New Vision U.S.A., Inc.'s Supplemental Response and Objections to Plaintiffs' Second Set of Interrogatories (with Exhibits A and B and 1–42), dated Mar. 30, 2005.

Nilar, L.J.H. Phutochemistry (2002), 60: 541–548. Xanthones from the heartwood of *Garcinia mangostana*.

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–81 are cancelled.

* * * * *